US00PP24525P3

(12) United States Plant Patent
Egger

(10) Patent No.: US PP24,525 P3
(45) Date of Patent: Jun. 3, 2014

(54) *HEUCHERA* PLANT NAMED 'FIRE ALARM'

(50) Latin Name: ***Heuchera* hybrid**
Varietal Denomination: Fire Alarm

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 172 days.

(21) Appl. No.: 13/507,202

(22) Filed: Jun. 12, 2012

(65) Prior Publication Data

US 2013/0333087 P1 Dec. 12, 2013

(51) Int. Cl.
*A01H 5/00* (2006.01)

(52) U.S. Cl.
USPC ..... Plt./440

(58) Field of Classification Search
CPC ..... A01H 5/02; A01H 5/12; A01H 5/025
USPC ..... Plt./440
See application file for complete search history.

*Primary Examiner* — June Hwu
(74) *Attorney, Agent, or Firm* — Klarquist Sparkman, LLP

(57) ABSTRACT

A new and distinct *Heuchera* plant characterized by large red spring and summer leaves to dark red fall and winter leaves, short flowering stems with showy white flowers, an excellent, multi-crowned, medium large mounding habit, and excellent vigor.

1 Drawing Sheet

Botanical denomination: *Heuchera* hybrid.
Variety designation: 'Fire Alarm'.

BACKGROUND OF THE INVENTION

The present invention relates to a new and distinct cultivar of *Heuchera* and given the cultivar name of 'Fire Alarm'. *Heuchera* is in the family Saxifragaceae. *Heuchera* 'Fire Alarm' came out of a planned breeding program to create large *Heuchera villosa* type red leaf *Heuchera*. This new cultivar originated from a cross between *Heuchera* K293-3, a proprietary non-commercial hybrid, as the seed parent, and *Heuchera* K428-2, a proprietary non-commercial hybrid, as, as the pollen parent.

Compared to the seed parent, *Heuchera* K293-3, the new cultivar has leaves red leaves rather than black and white rather than pink flowers.

Compared to the pollen parent, *Heuchera* K428-2, the new cultivar has red leaves rather than purple and white flowers rather than yellow green.

Compared to *Heuchera* 'Fire Chief', U.S. Pat. No. 21,880, the new cultivar has a much larger habit and leaves.

This new *Heuchera* is uniquely distinguished by:

1. large red spring and fall leaves to dark red summer and winter leaves,
2. short flowering stems with showy white flowers,
3. an excellent, multi-crowned, medium large mounding habit,
4. and excellent vigor.

This new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

FIG. 1 shows a two-year-old plant of *Heuchera* 'Fire Alarm' growing in the one gallon container outside in a full sun location in early May in Canby, Oreg.

DETAILED PLANT DESCRIPTION

The following is a detailed description of the new *Heuchera* cultivar based on observations of one and a half year-old specimens growing in one gallon containers outside in late May in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The *Royal Horticultural Society Colour Chart,* 2007 edition, 5$^{th}$ edition.

Plant:

*Form.*—Basal rosette, herbaceous perennial.
*Hardiness.*—USDA Zone 4 to 9.
*Size.*—26 cm tall from top of the foliage to the ground and 45 cm wide.
*Habit.*—Mounding.
*Vigor.*—Excellent.

Leaf:

*Type.*—Simple.
*Arrangement.*—Rosette.
*Shape.*—Broadly ovate to orbicular.
*Lobing/division.*—5 to 7 lobes, with shallow secondary lobes.
*Venation.*—Palmate.
*Margins.*—Crenate and slightly undulate.
*Apex.*—Mucronulate.
*Base.*—Cordate and overlapping.
*Blade size.*—Grows to 14 cm long and 14 cm wide.

*Surface texture.*—Glandular on top and bottom.

*Petiole description.*—Grows to 18 cm long and 4 mm wide, glandular hairs, Greyed Purple 186A.

*Leaf color.*—Color variable, depending on temperature and light conditions, topside spring and fall leaves Greyed Red 179A to 179B, bottom side Red Purple 60A; summer and winter leaves Greyed Purple 183A, bottom side Red Purple 60A; vein color is the same as the leaf.

Inflorescence:

*Size.*—Grows to 5.5 cm wide and 14 cm long.

*Type.*—Thyrse.

*Number of flowers per thyrse.*—About 50.

*Number of thyrse.*—About 8 in the first spring flush.

*Peduncle.*—Grows to 25 cm long, 3 mm wide at base, Greyed Purple 187C, glandular hairs.

*Pedicel.*—Variable in size, with glandular hairs, Greyed Purple 187B.

*Bloom period.*—May in Canby, Oreg.

Flower bud:

*Size.*—3 mm wide and 5 mm long.

*Description.*—Glandular puberulent, ovoid, down facing.

*Color.*—White NN155C.

Flower:

*Type.*—Perfect.

*Shape.*—Campanulate.

*Size.*—6 mm long and 4 mm wide.

*Corolla description.*—5 petals, 3 mm long and 0.4 mm wide, narrowly spatulate, margins entire, tip acute, glabrous top and glandular on bottom, White NN155C.

*Calyx description.*—Campanulate, 5 mm long and 4 mm wide, with 5 lobes divided ½ way to the base, each 1.5 mm wide and 2 mm long, glandular hairs outside and inside, tips obtuse, margin entire; color both sides White NN155B.

*Stamen description.*—5 in number, filaments 3 mm long, White NN155C, anthers 0.2 mm, Greyed Orange 164B, pollen none.

*Pistil description.*—1, 2-beaked, 6 mm long and 2.5 mm wide; White NN155C overall, ovary 2.5 mm long and 2.5 mm wide; style 3.5 mm long.

*Fragrance.*—None.

*Lastingness.*—Each thyrse blooms for about 3 weeks on the plant.

Fruit:

*Type.*—Two-beaked ovoid capsule.

*Fertility.*—Low.

*Color.*—Greyed Brown 199C.

Seed:

*Shape.*—Linear.

*Size.*—2 mm long.

*Color.*—Black 202A.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

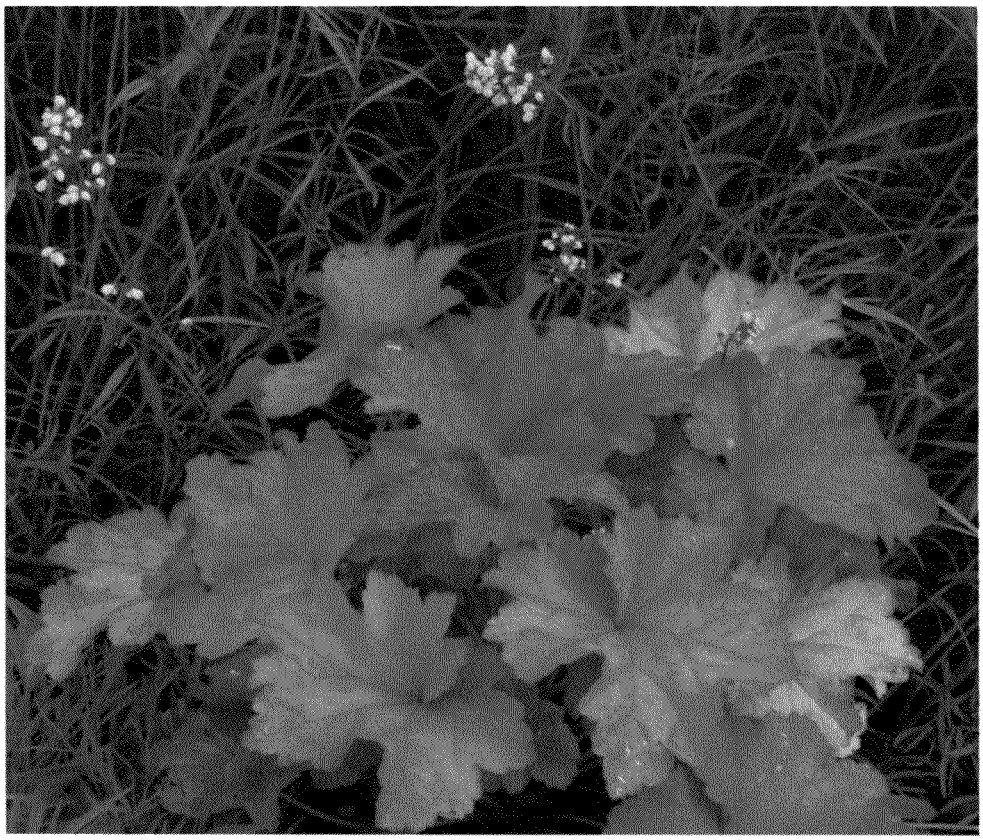

* * * * *